United States Patent
Paul (10) Patent No.: US 9,702,470 B2
(45) Date of Patent: Jul. 11, 2017

(54) VALVE ARRANGEMENT, APPARATUS AND METHODS OF OPERATION THEREOF

(71) Applicant: Horne Engineering Limited, Johnstone Renfrewshire (GB)

(72) Inventor: Graham Donald Paul, Johnstone Renfrewshire (GB)

(73) Assignee: Horne Engineering Limited, Johnstone Renfrewshire (GB)

( * ) Notice: Subject to any disclaimer, the term of this patent is extended or adjusted under 35 U.S.C. 154(b) by 0 days.

(21) Appl. No.: 14/762,741

(22) PCT Filed: Jan. 16, 2014

(86) PCT No.: PCT/GB2014/050116
§ 371 (c)(1),
(2) Date: Jul. 22, 2015

(87) PCT Pub. No.: WO2014/114914
PCT Pub. Date: Jul. 31, 2014

(65) Prior Publication Data
US 2015/0369382 A1   Dec. 24, 2015

(30) Foreign Application Priority Data

Jan. 23, 2013 (GB) .................................. 1301205.9

(51) Int. Cl.
*F16K 11/22* (2006.01)
*F16K 35/06* (2006.01)
(Continued)

(52) U.S. Cl.
CPC ................ *F16K 11/22* (2013.01); *A61L 2/04* (2013.01); *E03B 7/006* (2013.01); *E03C 1/04* (2013.01);
(Continued)

(58) Field of Classification Search
CPC ................................................ E03C 2201/30
(Continued)

(56) References Cited

U.S. PATENT DOCUMENTS 4,685,156 A     8/1987   Brabazon
5,050,640 A *   9/1991   Cowley ............... F24D 17/0073
                                                                       137/606
(Continued)

FOREIGN PATENT DOCUMENTS

CN      202203449 U     4/2012
CN      202469083 U    10/2012
(Continued)

OTHER PUBLICATIONS

English translation of FR 1228956 A provided by Proquest.com: "Adjusting device of fluid with compensated flow," Ericsson et al., Sep. 2, 1960.*
(Continued)

*Primary Examiner* — Kevin Joyner
*Assistant Examiner* — Holly Mull
(74) *Attorney, Agent, or Firm* — Drinker Biddle & Reath LLP (57) ABSTRACT

A valve arrangement comprises first and second valves mechanically interconnected for synchronous operation with one another so as to be switchable by a single action between first and second fluid flow configurations. The first configuration provides a first path for first fluid to flow from a first inlet to a first outlet and a second path for second fluid to flow from a second inlet to a second outlet. The second configuration provides paths for first fluid to flow from the first inlet to both the first and second outlets while closing the path from the second inlet. In one application, the arrangement allows a convenient method of disinfecting a water-consuming appliance such as a shower.

15 Claims, 7 Drawing Sheets

(51) Int. Cl.
  *E03C 1/04* (2006.01)
  *A61L 2/04* (2006.01)
  *F24D 17/00* (2006.01)
  *F24D 19/10* (2006.01)
  *G05D 23/13* (2006.01)
  *E03B 7/00* (2006.01)
  *F16K 37/00* (2006.01)
  *F16K 11/18* (2006.01)
  *E03C 1/02* (2006.01)

(52) U.S. Cl.
  CPC ............ *E03C 1/0408* (2013.01); *F16K 11/18* (2013.01); *F16K 35/06* (2013.01); *F16K 37/0016* (2013.01); *F24D 17/0073* (2013.01); *F24D 19/1051* (2013.01); *G05D 23/1353* (2013.01); *E03C 2001/026* (2013.01); *E03C 2201/40* (2013.01); *Y10T 137/0502* (2015.04); *Y10T 137/8158* (2015.04); *Y10T 137/86558* (2015.04); *Y10T 137/86566* (2015.04)

(58) Field of Classification Search
  USPC .......................................................... 422/38
  See application file for complete search history.

(56) References Cited

U.S. PATENT DOCUMENTS

| | | | | |
|---|---|---|---|---|
| 6,886,508 B1 * | 5/2005 | Luffy | ................ | F01M 1/18 |
| | | | | 123/198 B |
| 2011/0017325 A1 * | 1/2011 | Hoshi | ................ | G01F 1/36 |
| | | | | 137/595 |

FOREIGN PATENT DOCUMENTS

| | | | | |
|---|---|---|---|---|
| DE | 20300715 U1 | 5/2003 | | |
| EP | 1762769 A2 | 3/2007 | | |
| FR | 1228956 A | 9/1960 | | |
| FR | 2916033 A1 | 11/2008 | | |
| SE | WO 0161224 A1 * | 8/2001 | ............ | A61L 2/18 |
| WO | 2004048856 A1 | 6/2004 | | |
| WO | 2008116242 A1 | 10/2008 | | |

OTHER PUBLICATIONS

International Search Report dated Apr. 24, 2014 (PCT/GB2014/050116).

* cited by examiner

VALVE ARRANGEMENT, APPARATUS AND METHODS OF OPERATION THEREOF

FIELD

The invention relates to valve arrangements for water and other fluids. The invention may be applied, by way of example only, in sanitary and other installations where appliances use supplies of hot and cold water. The invention finds use in particular in providing for thermal disinfection of such appliances.

BACKGROUND

Many type of installation or appliance use water. For example, a shower or sink in a domestic or institutional setting, may use hot and cold water from supplies. The hot and cold water may be mixed by a simple mixing tap, or mixed by a special valve such as a thermostatic mixing valve or TMV. A TMV works by blending hot and cold water from their respective supply pipes to generate water at a preset temperature safe for use by humans. This preset temperature is invariably at a temperature that supports the rapid growth of bacteria. Chemical treatment regimes are sometimes favoured to kill the bacteria, but suitable chemicals tend to be powerful oxidisers, and can cause serious damage to brass components and elastomeric seals. They are also hazardous (e.g. toxic and/or corrosive) in their concentrated form, and therefore dangerous to transport and handle. Moreover, some organisms are resistant to chemicals. One reason for this may be that, where the organisms form a biofilm, for example, dead cells killed by the chemical agent can act as a shield for living layers beneath.

Heat is a reliable method of killing such bacteria, but that initially would appear to be an inappropriate method of killing bacteria in a TMV because the purpose of the TMV is to prevent scalding, and thus the valve never gets to the temperatures that would kill the bacteria.

This apparent conflict has previously been addressed in installations using electronically-controlled solenoid valves. The electronic controller sometimes has a "sterilise option" whereby solenoid valves controlling the water pathways are switched into a position such that the hot supply is internally fed around an appliance in such a way as to heat up the whole appliance. The outlet is then operated and flushes through with unblended hot water. This quickly heats up the whole product to hot water temperature, which should be sufficient to kill any bacteria present within around 5 minutes. However, it also carries the attendant risk of scalding to anyone who happens to be using the facility being sterilised at the time. It is therefore convention to do this at a time when no-one is likely to be using the facility, e.g. overnight. This activity may be initiated/activated by a control computer remote from the individual valves being sterilised, such as a BMS (Building Management System). An electronic thermal sterilising kit is available from Schell GmbH & Co. KG (Armaturentechnologie) of Olpe, Germany. See http://www.schell-armaturen.de/index.php?vw type=artikel&vw id=4431&struktur=1&praesenz=1 and the associated installation instructions that can be downloaded from there. Unfortunately, there is always the risk that one of the solenoid valves could jam, or leak, and that hot water could continue to flow into the cold water inlet of the product, creating a scald risk. There is also the risk that an electronic fault in the controller, or wiring, could permit the sterilise function to operate at an inappropriate time. The mere presence of this remotely operated capability represents a risk. The reliance on electronics also increases the skills required for installation and maintenance.

As an alternative solution, the present applicant has offered a Thermal Disinfection Kit for some valves. The Thermal Disinfection Kit comprises adaptors which fit into the strainer caps of the shower valve, and a hose to cross connect the supplies. In order to do this safely, it is necessary to first isolate the cold water supply, and keep it isolated during the disinfection procedure, which involves opening the Hot Water isolation valve, and then operating the outlet. Failure to do this properly in the correct sequence could result in the mixing valve not being sterilised properly, and also in hot water passing into the cold supply pipework. Fitting the current Thermal Disinfection Kit is inconvenient, requiring several steps, and handling of hot components. These drawbacks are tolerated as it is the only way that the desired outcome can be accomplished. On the other hand, many installations in general use are simply not properly disinfected because of the inconvenience and complexity of the process.

SUMMARY OF THE INVENTION

The invention in a first aspect provides a valve arrangement having first and second fluid inlets and first and second fluid outlets, the valve arrangement comprising first and second valves mechanically interconnected for synchronous operation with one another so as to be switchable by a single action between first and second fluid flow configurations, the first configuration providing a first path for first fluid to flow from the first inlet to the first outlet and a second path for second fluid to flow from the second inlet to the second outlet, the second configuration providing paths for first fluid to flow from the first inlet to both the first and second outlets while closing the path from the second inlet.

It will be seen below how such an arrangement solves the problem of more convenient and safe thermal disinfection in water-consuming appliances. The arrangement can be used for other purposes, however.

Said first and second valves may be three-way valves. In one such embodiment, the first three-way valve has first and second ports connected to the first inlet and first outlet respectively, the second three-way valve has first and second ports connected to the second inlet and second outlet respectively, and the first three-way valve has a third port connected to a third port of the second three-way valve. The first and second ports of each three-way valve may be in line with one another, while the third port is at right angles. This makes it convenient to connect the arrangement in supply lines. The first and second valves may be ball valves.

In some embodiments, said first and second valves are rotary valves connected by a multi-arm linkage. They may alternatively be connected by gears or other mechanisms for synchronising their rotation. In one embodiment, the first valve rotates by a half turn while the second valve rotates by either a quarter or three quarter turn, when moving between the first and second configurations.

The valve arrangement may be adapted for manual actuation, comprising a removable key for achieving said single operation by manual actuation, thereby to prevent accidental switching into the second configuration. In one embodiment, the key is not removable when the valve arrangement is in the second configuration.

Alternatively or in addition, the arrangement may include a warning indicator visible to prevent accidental use of an appliance when the device is in the second configuration.

In a convenient form, the first and second valves are formed by two substantially identical valve bodies. Said identical valve bodies may contain two identical moving valve parts.

The second configuration may provide a path from said first inlet to said second outlet that is more restricted than the path provided in said first configuration from said second inlet to said second outlet. This reduces wastage of fluid and/or running costs.

The invention further provides an apparatus comprising a valve arrangement as claimed in any preceding claim in combination with an appliance that consumes first and second fluids, the first and second outlets of the valve arrangement being connected respectively to first and second fluid inlets of the consuming appliance.

For thermal disinfection applications, the consuming appliance may be one operable to mix hot water from its first inlet with cold water from its second inlet to deliver water to a user at an intermediate temperature, the apparatus being operable with the valve arrangement in its second configuration to perform thermal disinfection of the appliance. In a representative application, the appliance is a shower installation.

The invention further provides a method of disinfecting a water-consuming appliance, the appliance having inlets for hot and cold water, the method comprising the steps of:
  installing a valve arrangement according to the first aspect o the invention as set forth above between hot and cold water supplies and hot and cold water inlets of the appliance;
  setting the valve arrangement to its second configuration so as to deliver hot water to both inlets of the appliance;
  running hot water through both inlets of the appliance for a period of time; and
  returning the valve arrangement to its first configuration for normal operation.

While the novel valve arrangement and methods have been developed initially for thermal disinfection of appliances connected to hot and cold water supplies, it may find application in other configurations and other applications. The invention in its broadest aspect is not limited to water-consuming installations or appliances, nor to appliances consuming hot and cold fluids. Even where the fluids are hot and cold, the arrangement may be installed and operated with the cold water as the first fluid and the hot water as the second fluid. In that case, the second configuration may be used for forced cooling (chilling) of the appliance or items fed by it, instead of heating for thermal disinfection. The skilled person can readily envisage a wide range of applications in chemical and food process industries, engine cooling systems. One or both of the fluids may be ingredients or products of the process, or they may be heat exchange fluids flowing through the apparatus to cool other parts or products.

Accordingly the invention yet further provides a method of operating a fluid-consuming appliance, the appliance having inlets for first and second fluid, the method comprising the steps of:
  installing a valve arrangement according to the first aspect of the invention as set forth above between first and second fluid supplies and first and second fluid inlets of the appliance;
  setting the valve arrangement to its second configuration so as to deliver first fluid to both inlets of the appliance;
  running first fluid through both inlets of the appliance for a period of time; and
  returning the valve arrangement to its first configuration for normal operation.

BRIEF DESCRIPTION OF DRAWINGS

Embodiments of the invention will now be described, by way of example only, by reference to the accompanying drawings, in which.

DETAILED DESCRIPTION OF EXEMPLARY EMBODIMENTS

Figure 1:
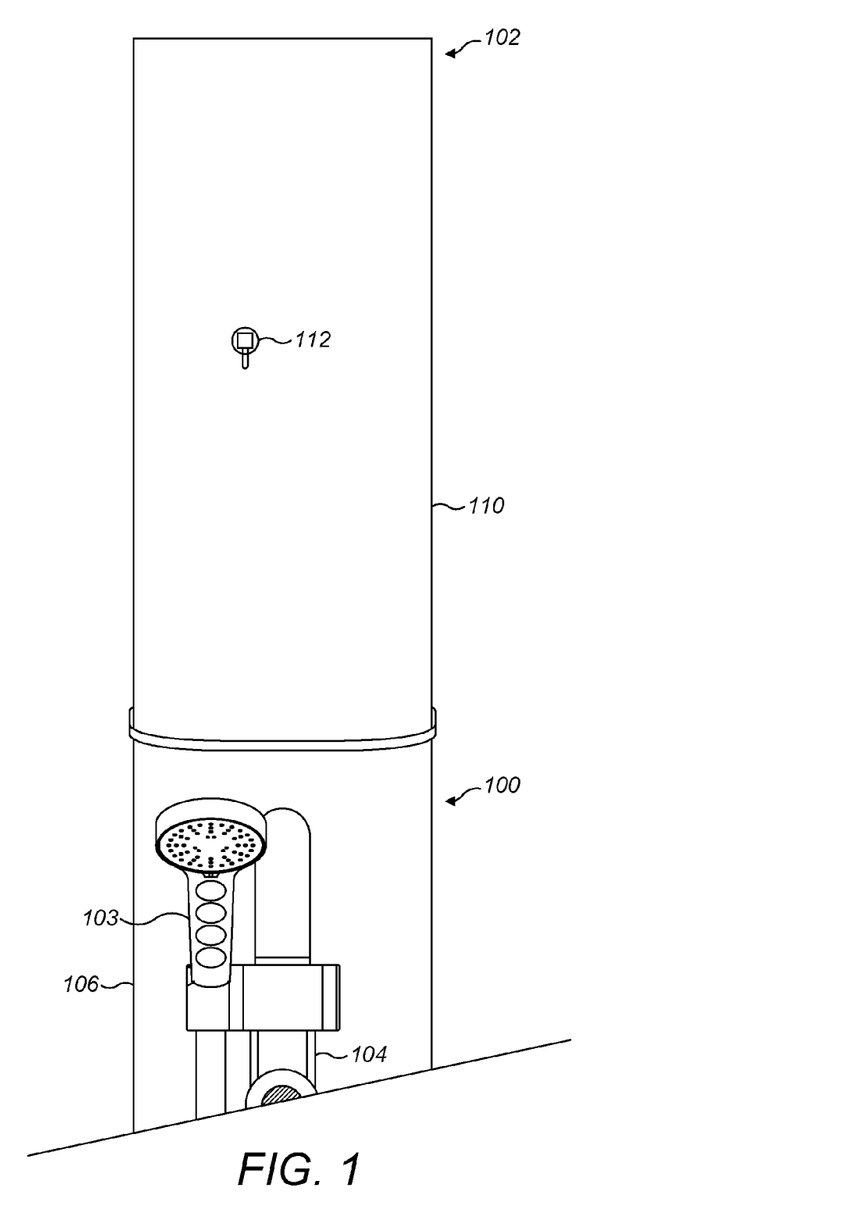
FIG. 1 is an external view of a disinfection adaptor fitted above a shower unit, in accordance with one embodiment of the invention.

FIG. 1 shows a top part of a shower unit 100, above which is mounted a novel disinfection adaptor 102, which forms an embodiment of the present invention. The shower unit can be of any conventional form, comprising for example a shower head 103 mounted adjustably on a rail 104. A mixing valve and associated plumbing are contained within a housing 106, to deliver a mixture of hot and cold water to a safe and comfortable temperature for supply to shower head 103. The mixing valve may be for example a thermostatic mixing valve, for optimum regulation of the temperature of the shower. In outward appearance, disinfection adaptor 102 comprises simply a housing 110 and keyhole 112. The housings 106 and 110 are matched in appearance and hide the working parts of the shower and disinfection adapter, as well as the associated pipework. Alternatively, of course the housing may be omitted and the workings exposed. The shower is used in this description as just one example of an appliance consuming hot and cold water. The shower may be installed in a domestic or institutional setting.

Figure 2:
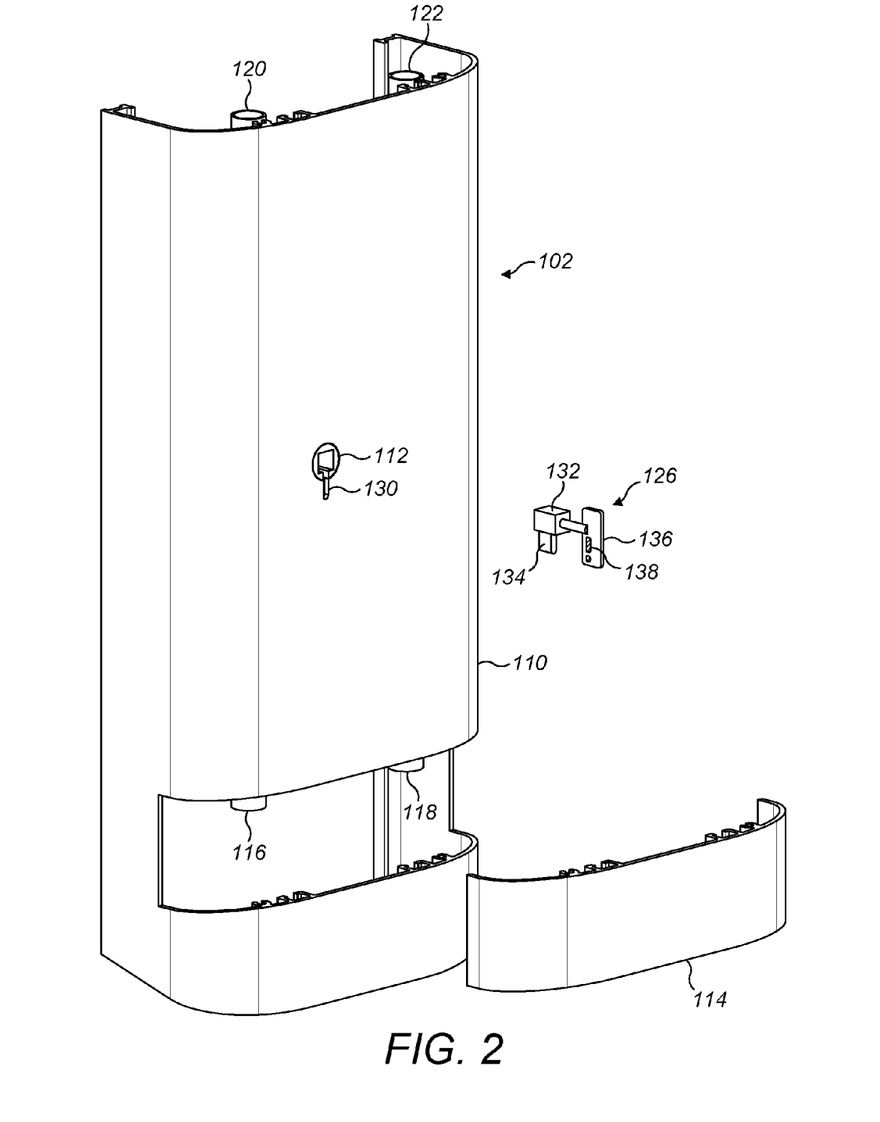
FIG. 2 is an external and partly disassembled view of the disinfection adaptor of FIG. 1.
Figure 3:
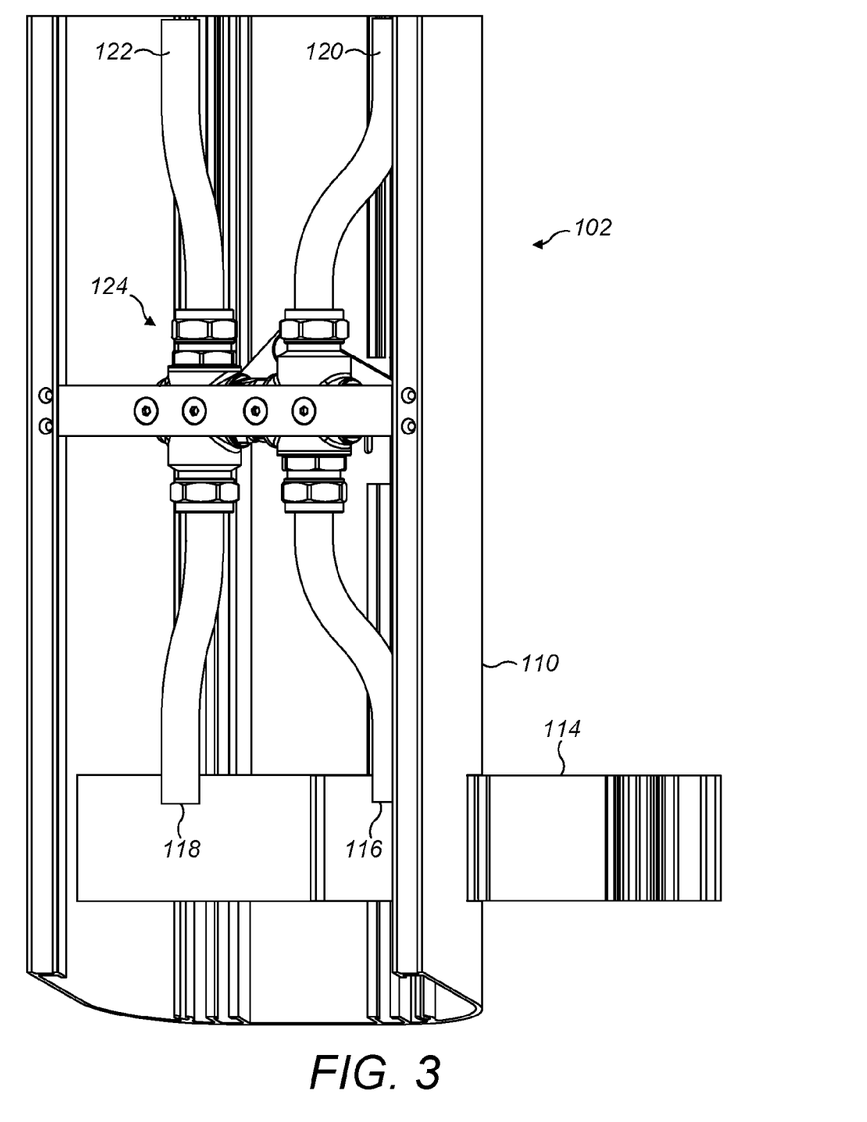
FIG. 3 is a rear view of the disinfection adaptor.

FIG. 2 is a view of the disinfection adaptor 102 prior to installation. FIG. 3 is a rear view of the same adaptor 1 and 2, and should be viewed together with FIG. 2. A part 114 of the housing 110 has been removed to assist installation. On removal of this housing part, one can access first and second feed pipes 116 and 118 that are connected to corresponding inlets of the shower unit 100, or other appliance. These feed pipes form outlets of the adapter. Feed pipe 116 is positioned for connection to a hot supply inlet of the appliance (not shown), while feed pipe 118 is positioned for connection to the cold supply inlet of the appliance (also not shown). At the top side of the adaptor 102, first and second supply pipes 120 and 122 are provided for connection to hot and cold water supplies, respectively. As can be seen in the back view of FIG. 3, a valve arrangement 124 is connected between the supply pipes 120, 122 and the feed pipes 116 and 118. Valve arrangement 124 is operable by a key 126 (FIG. 2), via keyhole 112. The purpose of the valve arrangement and key 126 is to switch the installation between (i) a normal operating mode, in which hot water and cold water are fed from respective supplies to the shower unit to be mixed and released in a controlled manner by shower head 103, and (ii) a disinfection mode, in which hot water from supply inlet 120 is fed to both the hot and cold inlets of the shower unit, in order to raise its temperature for disinfection. More detail of this valve arrangement and its operation will be provided later.

Key 126 and keyhole 112 may take any appropriate form. In the embodiment illustrated, keyhole 112 is associated with a slot 130 in a housing 110. The matching key has a body part 132 for entering the main part of the keyhole and turning moving parts within the valve arrangement. A projection 134 is also provided on the key which, only in a first orientation, can enter the slot 130. This orientation, being the one illustrated in FIG. 2, corresponds to the normal operating mode. For disinfection operation, the key is turned to another position, in which it cannot be withdrawn because the projection 134 is not aligned with the slot 130. Key 126 has a prominent and brightly coloured handle 136, marked with warnings 138. These are to caution against use of the shower when the valve arrangement is set to the disinfection mode. A more sophisticated form of key and lock can be used, if desired. The simple slot and projection provide a simple illustration of the principle.

Figure 4A:
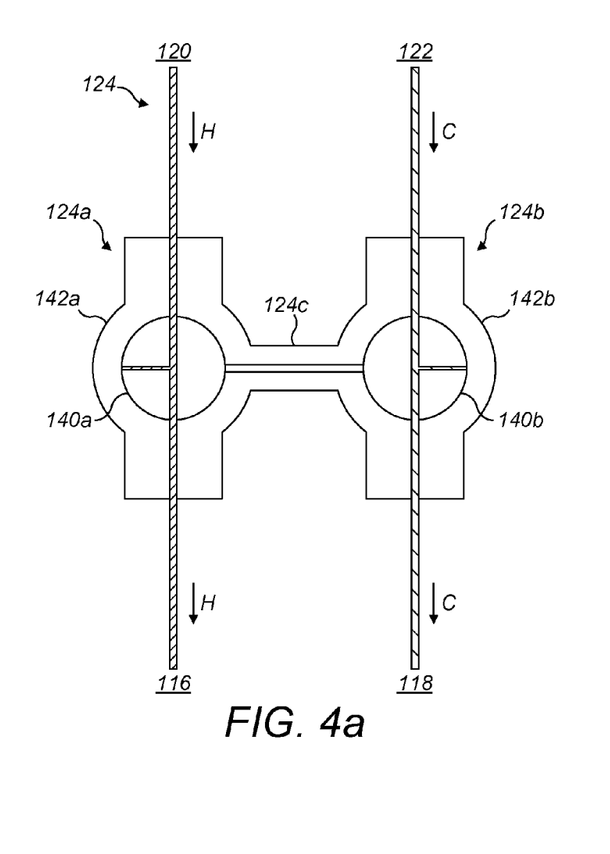
FIGS. 4a and 4b show in schematic form the form and function of the disinfection adaptor in first and second modes of operation.
Figure 4B:
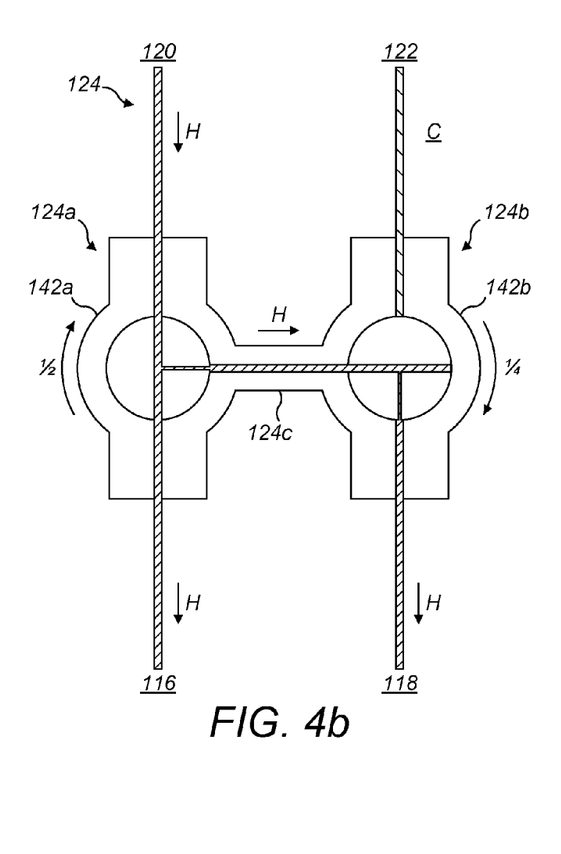

FIGS. 4a and 4b show schematically the form and operation of the valve arrangement 124 in the disinfection adaptor of 102 in one embodiment of the invention. The view corresponds to that of FIG. 2, i.e. the front view of the adaptor. The positions of the hot and cold feed pipes 116, 118 and the hot and cold supply pipes 120, 122 are indicated. Hatched areas show the paths of hot and cold water in the different modes of operation, using denser hatching for the hot water and lighter hatching for the cold.

Valve arrangement 124 in this example comprises two individual valves 124a and 124b. Each valve is a 3-way valve, with a main path running from top to bottom, as shown in the diagram, and a secondary path leaving at right angles. The main path of first valve 124a is connected between the hot supply inlet 120 and the hot feed pipe 116. The main path of the second valve 124b is connected between the cold supply inlet 122 and the cold feed pipe 118. The secondary inlet/outlet of the valves 124a and 124b are connected together by a cross-connection 124c.

Each valve 124a, 124b comprises a moveable valve part 140a, 140b, mounted in a valve body 142a, 142b. The valves in this example are operated by rotation, and an example based on this principle will be illustrated in more detail later. The valves may in principle be implemented instead as sliding valves, for example, without deviating from the principles of operation described. Each valve part 140a, 140b provides channels that can be aligned in different ways with ports in the corresponding body 142a, 142b, so as to connect the main and secondary flow paths of the valves according to the desired mode of operation.

It will also be noted that valves 124a, 124b and the individual parts in the described embodiments are of identical form to one another, but mounted anti-parallel (that is, with 180 degrees rotation). It is convenient for the manufacture and maintenance of the disinfection adaptor to use as few different parts as possible. On the other hand, the same functionality could be implemented using different designs of parts for the two valves, and/or using a single body for both valves.

Figure 5:
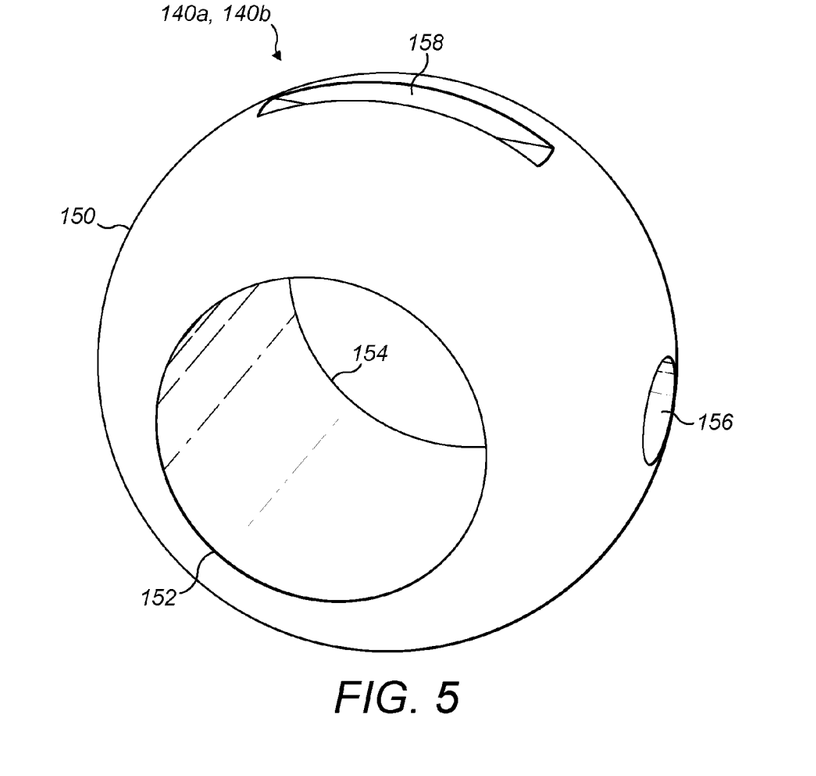
FIG. 5 shows a valve ball used in an embodiment of the disinfection adaptor.

FIG. 5 illustrates an example of a ball that can be used as one of the moving valve parts 140a, 140b in a practical embodiment of the valve arrangement shown in FIGS. 4a and 4b. The ball comprises a spherical body 150, formed with large openings 152, 154 opposite sides, connected to form a main flow channel through the ball 150. A smaller orifice 156 is formed, connecting with the main passage, to allow more restricted fluid flow. A slot 158 is formed in the ball 150, to allow rotation of the ball, to position the openings 152, 154, 156 against different ports in a valve body. It will be understood that a ball valve is merely one example of the type of valve that may be used, and one which is very well known and understood, and economic to implement. Other types of rotary valves, as well as slide valves, disc valves and the like may be adapted for use in embodiments of the invention, as desired.

Figure 6A:
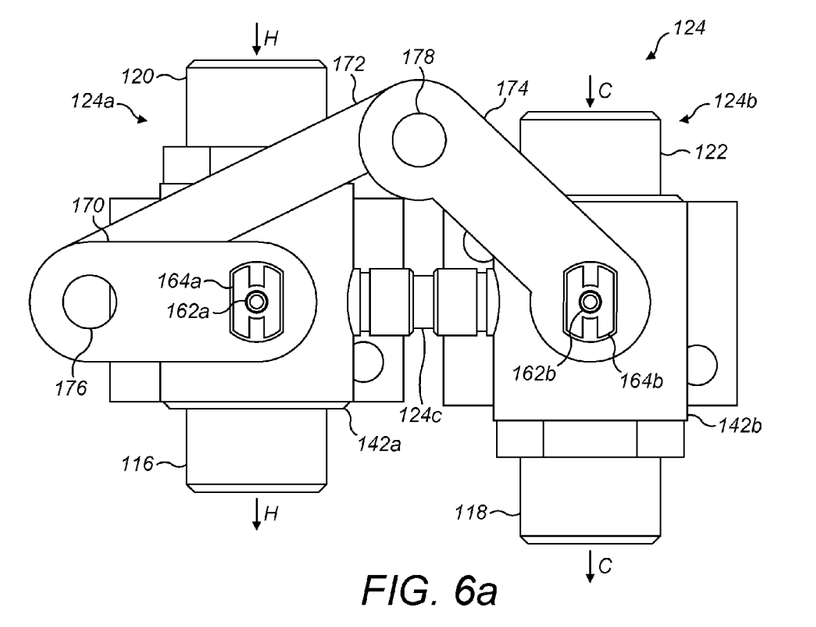
FIGS. 6a and 6b show a practical embodiment of a disinfection adaptor according to an embodiment of the invention, in the first and second configurations.
Figure 6B:
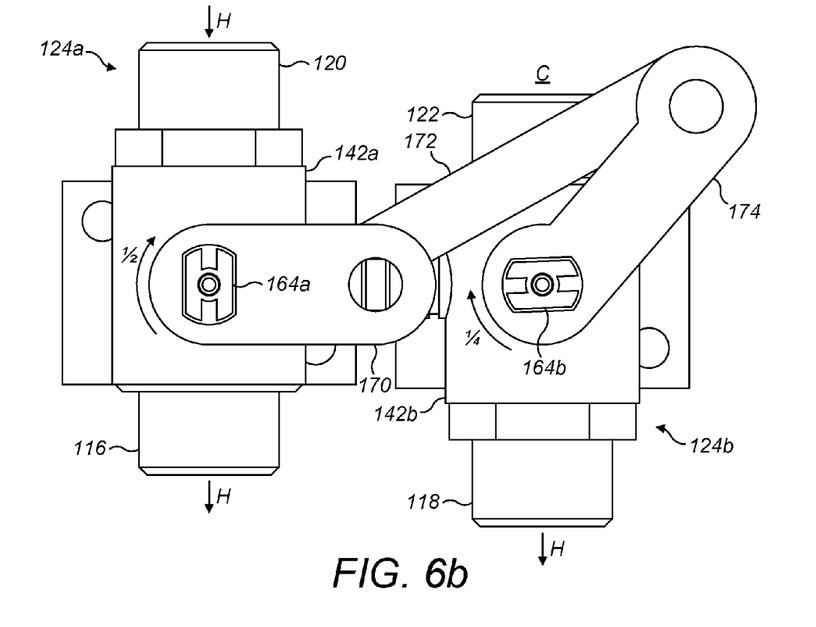

Referring now to FIGS. 6a and 6b, we see the valve arrangement 124 in a practical embodiment. FIG. 6a shows the valve in normal mode while FIG. 6b shows it in disinfection mode, just like FIGS. 4a and 4b. Individual valves 124a and 124b are connected between the inlet pipes 120, 122 and the feed pipes 116, 118, with a bridging conduit 124c between them. Each valve 124a, 124b comprises an identical valve body 142a, 142b. Within each body 142a, 142b is a moving part 140a, 140b, formed in this example by a ball of the type illustrated in FIG. 5. Again, this arrangement allows the use of identical parts for the two valves 124a, 124b, mounted anti-parallel, that is rotated by 180 degrees, but this is not essential.

Bridging conduit 124c can be made from material that is a poor thermal conductor so as to minimise heat transfer by conduction between the valves 124a and 124b, when the appliance is in normal use. A suitable material may be a polymer, for example.

Within each valve body 142a, 142b, a moving valve part (140a, 140b, not shown in FIGS. 6a, 6b) is housed, to control the flow of fluid between ports in the valve body, and consequently between the various supply and feed pipes 116 to 122. Each valve has a respective drive shaft 162a, 162b and drive head 164a, 164b. The moving valve part within each valve body has for example the form of the ball shown in FIG. 5. The drive shaft 162a thus engages with slot 158, so that the ball 150 may be turned by applying torque to the drive head 164a, 164b. The drive heads of the two valves 124a and 124b are mechanically coupled so that they rotate synchronously with one another. In the embodiment shown, this is achieved by a four bar linkage mechanism comprising three link arms, 170, 172 and 174. Link arm 170 engages drive head 164a of first valve 124a at one end and is connected by a pivot 176 to the second link arm 172, at its other end. A second end of link arm 172 is connected by a pivot 178 to the third link arm 174. A second end of link arm 174 is keyed to drive head 164b of the second valve 124b.

The angles and lengths of the arms are such that a half turn of the first valve drive head 164a is always associated with a quarter turn of the second valve drive head 164b in the same rotational direction, giving the two operating positions shown in the FIGS. 6a and 6b. The orientations of the moving valve parts 140a, 140b within the two valves are such that this movement causes the internal flow parts to switch between the normal mode and the disinfection mode, just as illustrated schematically in FIGS. 4a and 4b, respectively. Referring also to FIGS. 1 to 3, the first valve drive head 164a is driven by the key 126 in the keyhole 112, so that the half turn of the key will cause a half turn of the valve moving pat 140a.

Referring now to the operation of the valve arrangement 124 forming the disinfection adapter 102, in the "normal" configuration (for normal use of the shower), the hot and cold water flows unmodified and unimpeded through the valves 124a, 124b respectively and into the connected appliance, as though the adapter was not present. This is the condition illustrated in FIGS. 4a and 6a. Dense hatching and the letter H represent hot water flow, lighter hatching and the letter C represents cold water flow. Of course the valve arrangement by itself does not distinguish between hot and cold water. It is only when connected correctly in a plumbing installation that the terms hot and cold become literally true.

In the case of the ball valve, the two supplies pass straight through the respective balls and into the shower. The side port on each of the three-port balls faces outwards, where they are sealed off and no flow is possible through the side ports. The bridging conduit 124c is isolated by seals within the valves.

Switching to "Disinfection Mode" involves rotating the valves to put the valve arrangement 124 into the configuration shown in FIG. 4b or 6b. In this configuration the valves divert hot water through the additional side port of valve 124a through valve 124b and into the cold inlet of the shower. When the shower 100 is run, this configuration puts hot water into both the hot and cold ports of the shower mixing valve, and causing the mixing valve and associated pipework to rise to a temperature that will kill the target bacteria.

A key aspect of the design is that the drive to the pair of valves is achieved by a single operator action. Rotating the "driven" valve by a lower rotation than the "driving" valve helps reduce the torque required to actuate the device by making use of mechanical advantage.

The arrangement illustrated enables more convenient and reliable disinfection than known alternatives. Beneficial aspects of the described embodiments include:

a) A mechanical device may be preferred to electronics. Solenoid valves make implementing this kind of function relatively easy. A few lines of code in software would permit the configuration of the valves to be set. However, solenoid valves have recently been associated with problems related to harbouring bacteria themselves. Also, to install and maintain such a system would require a wider range of skills: should it be done by a plumber or an electrician, or both? The mechanical arrangement is simple and straightforward, and is made from parts, materials and technology that plumbers use on a daily basis. It is also 100% intuitive.

b) Single point actuation in a mechanical device. The lever actuation of the second valve from the user operation of the first eliminates the necessity to exercise skill to set valves in a particular sequence to achieve the desired result. It is foolproof. If the arrangement did not feature the synchronised operation of the valves, it would be necessary to position the first valve, and then position the second valve in a different position from the first in order to achieve the desired objective. After use, each valve would require to be independently reset, in a particular sequence to ensure that the hot and cold supplies were never cross-connected.

c) The valve arrangement is located directly above the shower being protected, so the person switching to the Disinfection mode is at the shower being disinfected and can thus prevent anyone from inadvertently using it.

d) The valve arrangement provides double isolation of the hot and cold supply from each other when the device is not in use. There are two closed valves between the hot supply pipework and the cold supply pipework during normal operation, thus ensuring that the isolation of the two supplies is not compromised by the invention.

e) Visible warning is provided on the front of the panel when the invention is in use. A high visibility interlocked handle (key 126) would be protruding from the casing providing a visible warning that the shower was being "used". This is especially important when it is in the "Disinfection" position, and the shower is thus putting out scalding hot water. For added safety the illustrated key further cannot be removed until the arrangement returns to the Normal configuration.

Figure 7A:
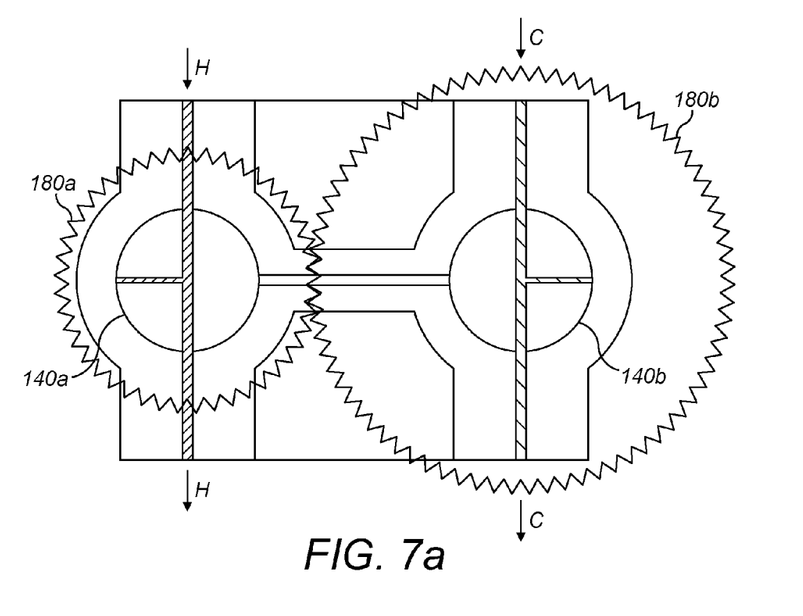
FIGS. 7a and 7b show schematically the operation of a second embodiment of the disinfection adaptor, using gears instead of linkages.
Figure 7B:
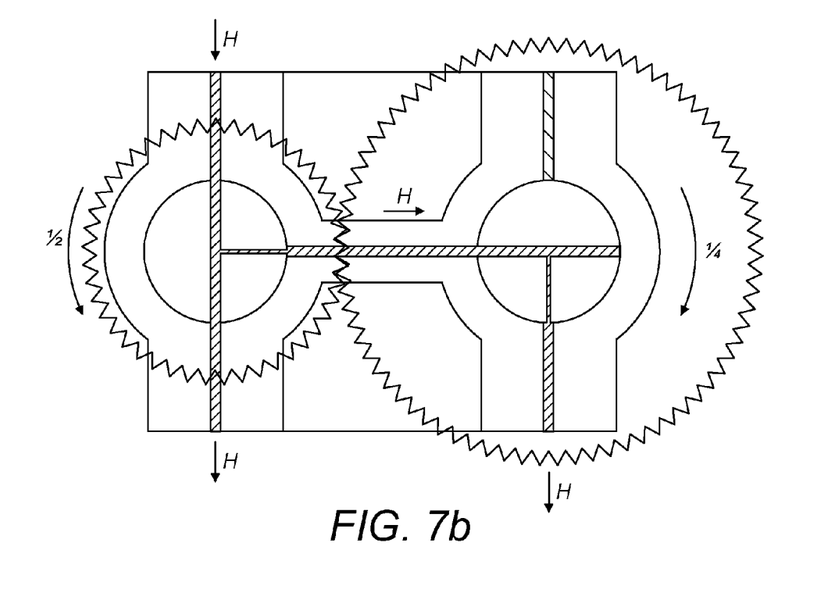

The movement of the two valves 124a, 124b can be synchronised by linkages as illustrated in FIG. 6a, 6b, or in other ways. For example, FIGS. 7a and 7b show schematically an embodiment in which movement of the valve parts 140a, 140b is synchronised by appropriately sized gears, 180a and 180b. Because the gear mechanism reverses the direction of rotation between the first and second valves, the half turn rotation of the key in this embodiment is in the opposite direction to that shown in the embodiment of FIGS. 6a, 6b. Other forms of linkage that may achieve the same synchronisation are full or partial segment gears, chain and sprocket, toothed drive belt, levers, cranks and cams, or any combination of these.

Any of these means would provide for the hot valve to be turned by 180 degrees rotation, and the cold valve to be turned simultaneously by 90 degrees rotation. In another version with differential rotation achieved by gears, it could be easier for the 124b to rotate by three quarters of a turn (270 degrees) in an anticlockwise direction, rather than by a quarter turn in a clockwise direction because of the rotational reversal associated with a pair of gears. In such a case, it may be preferred to drive the valve 124b by the user input, and have the "Hot" valve turned by the mechanical linkage. This would avoid the torque-multiplying effect of trying to drive one of the valves through a speed-increasing gear ratio. On the other hand, a three-quarter turn is a less intuitive movement for users to understand and implement reliably.

Numerous variations and modifications are possible, without departing from the basic principles of the embodiments described above. As has already been mentioned, the mechanical synchronisation of movements of the first and second valves may be achieved in a number of different ways, not only by linkages or gears.

While the valves in these examples have been shown with the "normal" parts flowing straight through, and "disinfection" parts branching at right angles, this is only one possible configuration. In other embodiments, the main flow parts could be at right angles, or any other angle. Providing the flow parts in a straight through form allows the adaptor to be connected in line, including by retro-fitting to an existing installation, without disrupting the arrangement of the water supplies. The straight through arrangement also simplifies incorporating the valve arrangement into future designs of appliances and/or installations.

It will be understood that the arrangement is designed to form a permanent part of an appliance or installation, in contrast to the known thermal disinfection adaptor kit, described in the introduction. While the adaptor has been described as an add-on to a shower unit, it may of course also be applied to any sanitary installation or other water-consuming appliance having hot and cold supplies, or any food processing or industrial installation requiring disinfection. While the apparatus has been shown in the form of a disinfection adaptor that can be added to a shower unit, with or without a degree of cosmetic matching, the valve arrangement 124 can of course be integrated into the body of the shower unit or any appliance. Instead of providing a valve arrangement to protect a single shower unit, the same valve arrangement could be provided at the supply side of a plurality of showers and/or sinks etc. These can be disinfected in parallel or by turns, through the shared valve arrangement. It will be understood that the valve arrangement in any of these embodiments is designed to form a permanent part of an appliance or installation, in contrast to the known thermal disinfection adaptor kit, described in the introduction.

While operation has been shown in this example by a key having a projection to prevent removal except in the "normal" operating position, other forms of safety mechanism and other forms of actuating handle may be readily envisaged. Instead of a key, a fixed handle, screwdriver slot or the like can be used. Different implementations of a visual warning can be provided, to discourage anyone from using the shower or other appliance while the hot water is fed to both outlets. It may also be envisaged that the actuating handle or other part will project so much that it physically obstructs use of the shower or other appliance.

Instead of a manual operation, an electric motor or other motor could be used to drive the arrangement between the normal and disinfection configurations. The manual drive has advantages of low cost and low complexity, as well as having the safety benefit of requiring the operator to be physically present to inspect the installation and prevent accidental use of the shower in the wrong mode. Compared with known electrical installations, there is still the benefit that only a single action is required, and not synchronisation of several solenoids or motors.

While the novel valve arrangement and methods have been developed initially for thermal disinfection of appliances connected to hot and cold water supplies, it may find application in other configurations and other applications. The invention in its broadest aspect is not limited to water-consuming installations or appliances, nor to appliances consuming hot and cold fluids. Even where the fluids are hot and cold, the arrangement may be installed and operated with the cold water as the first fluid and the hot water as the second fluid. In that case, the second configuration may be used for forced cooling (chilling) of the appliance or items fed by it, instead of heating for thermal disinfection. The skilled person can readily envisage a wide range of applications in chemical and food process industries, engine cooling systems, just by way of example. One or both of the fluids may be ingredients or products of the process, or they may be heat exchange fluids flowing through the apparatus to cool other parts or products. The implementer of the system will know how to adapt the scale and materials of the various parts to suit the different fields of application.

The above and other modifications and variations are readily envisaged by the skilled reader, without departing from the spirit and scope of the invention.

The invention claimed is:

1. An apparatus comprising a thermal disinfection apparatus in combination with a sanitary installation that consumes hot and cold water,
   the thermal disinfection apparatus comprising a valve arrangement having a first hot water inlet and a second cold water inlet and first and second water outlets, the valve arrangement comprising first and second valves mechanically interconnected for synchronous operation with one another so as to be switchable by a single action between first and second fluid flow configurations, the first configuration providing a first path for hot water to flow from the first hot water inlet to the first water outlet and a second path for cold water to flow from the second cold water inlet to the second water outlet, the second configuration providing a path for hot water to flow from the first hot water inlet to the first water outlet and a path for hot water to flow from the first hot water inlet through a bridging conduit to the second water outlet while closing the path from the second cold water inlet to the second water outlet, wherein the first valve and the second valve are thermally isolated from each other and have no mutually connecting portion within the bridging conduit,
   the first and second water outlets of the valve arrangement being connected respectively to a first hot water inlet and a second cold water inlet of the sanitary installation,
   wherein said sanitary installation is operable to mix hot water from its first hot water inlet with cold water from its second cold water inlet to deliver water to a user at an intermediate temperature, the apparatus being operable with the valve arrangement in its second configuration to perform thermal disinfection of the sanitary installation.

2. The apparatus as claimed in claim 1 wherein said first and second valves are three-way valves.

3. The apparatus as claimed in claim 2 wherein the first three-way valve has first and second ports connected to the first hot water inlet and first water outlet respectively, the second three-way valve has first and second ports connected to the second cold water inlet and second water outlet respectively, and the first three-way valve has a third port connected to a third port of the second three-way valve.

4. The apparatus as claimed in claim 2 wherein the first and second ports of each three-way valve are in line with one another, while the third port is at right angles.

5. The apparatus as claimed in claim 1 wherein said first and second valves are ball valves.

6. The apparatus as claimed in claim 1 wherein said first and second valves are rotary valves connected by a multi-arm linkage.

7. The apparatus as claimed in claim 1 wherein said first and second valves are rotary valves mechanically connected so that the first valve rotates by a half turn while the second valve rotates by either a quarter or three quarter turn, when moving between the first and second configurations.

8. The apparatus as claimed in claim 1, adapted for manual actuation, comprising a removable key for achieving said single operation by manual actuation, thereby to prevent accidental switching into the second configuration.

9. The apparatus as claimed in claim 8 wherein said key is not removable when the valve arrangement is in the second configuration.

10. The apparatus as claimed in claim 1 including a warning indicator visible to prevent accidental use of an appliance when the device is in the second configuration.

11. The apparatus as claimed in claim 1 wherein said first and second valves are formed by two substantially identical valve bodies.

12. The apparatus as claimed in claim 11 wherein said identical valve bodies contain two identical moving valve parts.

13. The apparatus as claimed in claim 1 wherein the second configuration provides a path from said first hot water inlet to said second water outlet that is more restricted than the path provided in said first configuration from said second cold water inlet to said second water outlet.

14. The apparatus as claimed in claim 1 wherein said sanitary installation is a shower installation.

15. A method of disinfecting a sanitary installation, the sanitary installation having inlets for hot and cold water, the method comprising the steps of:
  providing an apparatus comprising a thermal disinfection apparatus in combination with a sanitary installation as claimed in claim 1;
  connecting the first hot water inlet and second cold water inlet of the thermal disinfection apparatus to hot and cold water supplies respectively;
  setting the valve arrangement to its second configuration so as to deliver hot water to both inlets of the appliance;
  running hot water through both inlets of the appliance for a period of time; and
  returning the valve arrangement to its first configuration for normal operation.

* * * * *